US00PP30360P2

(12) United States Plant Patent
Kardos et al.

(10) Patent No.: US PP30,360 P2
(45) Date of Patent: Apr. 9, 2019

(54) ***LAGERSTROEMIA* PLANT NAMED 'BAILLAGONE'**

(50) Latin Name: ***Lagerstroemia* hybrid**
Varietal Denomination: Baillagone

(71) Applicant: Bailey Nurseries Inc, Newport, MN (US)

(72) Inventors: Joshua H. Kardos, Asheville, NC (US); Michael A. Dirr, Bogart, GA (US); Rhonda Helvick, Madison, GA (US); Oren McBee, Bishop, GA (US)

(73) Assignee: BAILEY NURSERIES INC., Newport, MN (US)

( * ) Notice: Subject to any disclaimer, the term of this patent is extended or adjusted under 35 U.S.C. 154(b) by 0 days.

(21) Appl. No.: 15/732,409

(22) Filed: Nov. 7, 2017

(51) Int. Cl.
*A01H 5/02* (2018.01)

(52) U.S. Cl.
USPC ..... Plt./252

(58) Field of Classification Search
USPC ..... Plt./226, 252
See application file for complete search history.

*Primary Examiner* — Susan McCormick Ewoldt
*Assistant Examiner* — Karen M Redden
(74) *Attorney, Agent, or Firm* — Penny J. Aguirre

(57) ABSTRACT

A new cultivar of *Lagerstroemia* plant named 'Baillagone' that is characterized by its oval shaped, compact, tight plant habit of intermediate stature, its foliage that is dark reddish green in color in summer, its flower buds that are yellow-green and tinged with red at apex, its flowers that are large in size and white in color, and its high resistance to powdery mildew and Cercospora leaf spot.

2 Drawing Sheets

Botanical classification: *Lagerstroemia* hybrid.
Variety denomination: 'Baillagone'.

BACKGROUND OF THE INVENTION

The present invention relates to a new and distinct cultivar of *Lagerstroemia* of hybrid origin. The new *Lagerstroemia* will hereafter be referred to by its cultivar name, 'Baillagone'. 'Baillagone' is a new cultivar of crape myrtle grown for use as an ornamental landscape plant.

The new cultivar was derived from a controlled breeding program conducted by the Inventors in Watkinsville, Ga. The objective of the breeding program is to develop a new cultivar of crape myrtle with an intermediate plant habit, dark foliage and white flowers.

'Baillagone' arose from a cross-made in 2012 between *Lagerstroemia* 'PIILAG-IV' (U.S. Plant Pat. No. 25,478) as the female parent and *Lagerstroemia* 'PIILAG-I' (U.S. Plant Pat. No. 23,168) as the male parent. 'Baillagone' was selected as a single unique plant in 2014 from amongst the seedlings derived from the above cross.

Asexual propagation of the new cultivar was first accomplished by semi-hardwood stem cuttings by one of the Inventors in Watkinsville, Ga. in 2014. Asexual propagation by semi-hardwood stem cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Baillagone' as a unique cultivar of *Lagerstroemia*.

1. 'Baillagone' exhibits an oval shaped, compact, and tight plant habit of intermediate stature.

2. 'Baillagone' exhibits foliage that is dark reddish green in color in summer.
3. 'Baillagone' exhibits flower buds that are yellow-green and tinged with red at apex.
4. 'Baillagone' exhibits flowers that are large in size and white in color.
5. 'Baillagone' exhibits high resistance to powdery mildew and Cercospora leaf spot.

'PIILAG-IV', the female parent of 'Baillagone', differs from 'Baillagone' in having an upright growth habit, dark maroon purple foliage and red flower buds that open white with hints of pink in color. 'PIILAG-I' , the male parent of 'Baillagone', differs from 'Baillagone' in having a rounded and dwarf plant habit, foliage that is green in color and flower buds that are yellow-green in color with no red coloration. 'Baillagone' can also be compared to the *Lagerstroemia* cultivar 'Sarah's Favorite' (not patented). 'Sarah's Favorite' is similar to 'Baillagone' in having clear white flowers. 'Sarah's Favorite' differs from 'Baillagone' in having a taller plant height and foliage that is green in color.

BRIEF DESCRIPTION OF THE DRAWINGS

The accompanying colored photographs illustrate the overall appearance and distinct characteristics of the new 'Baillagone'. The photographs were taken of a 4 year-old plant of 'Baillagone' as grown outdoors in full sun in Watkinsville, Ga.

The photograph in FIG. 1 provides a side view of 'Baillagone' in bloom.

Figure 1:
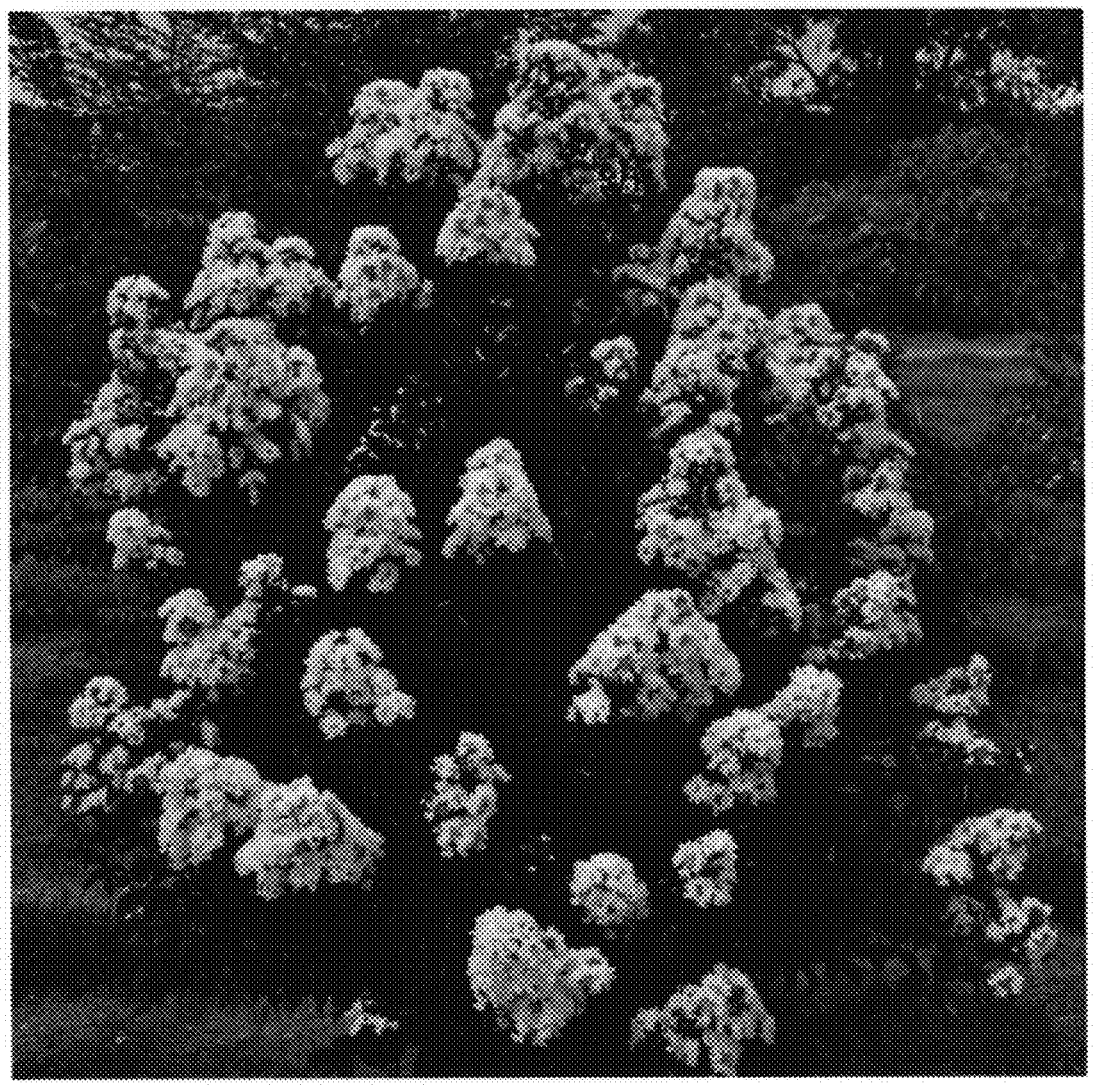
Figure 2:
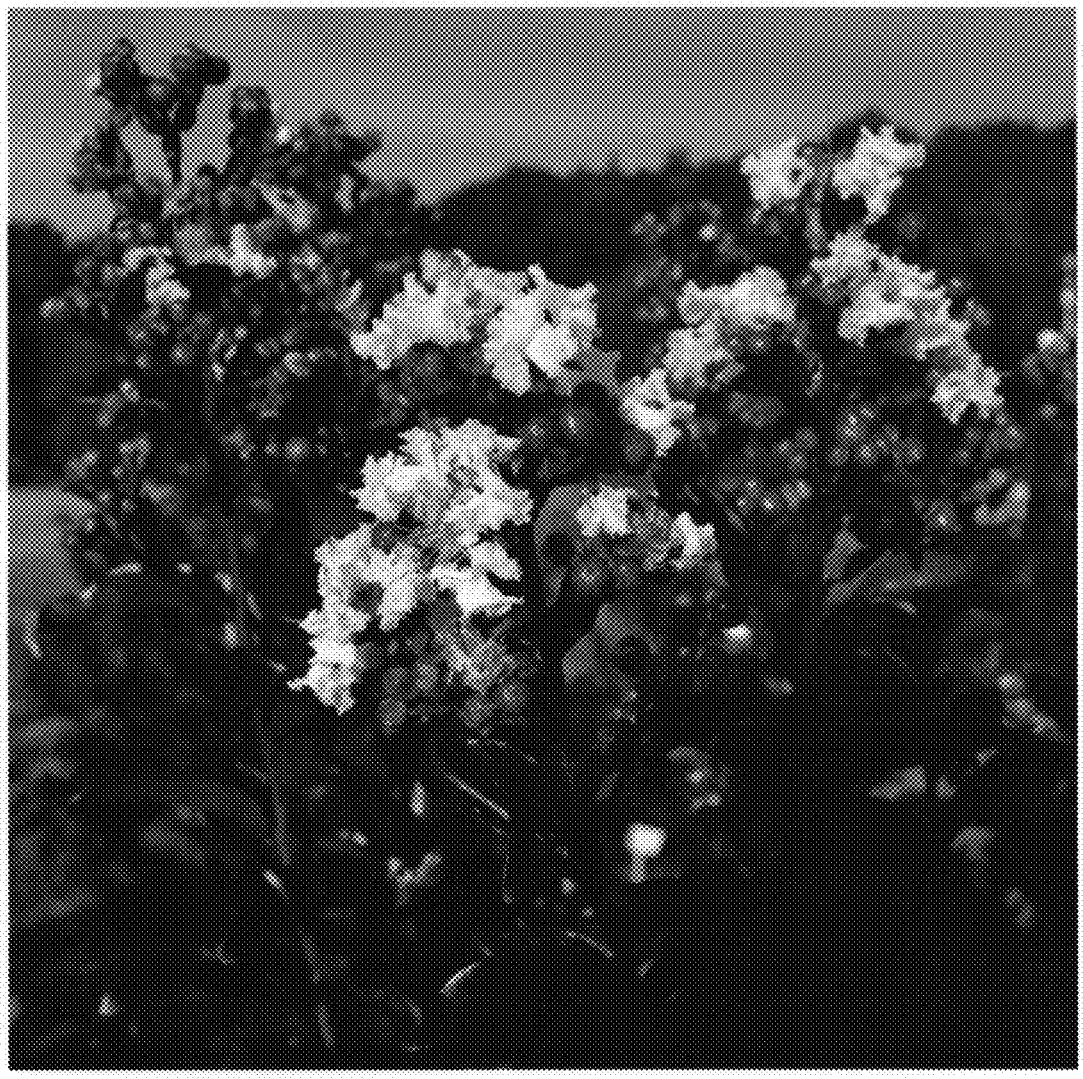

The photograph in FIG. 2 provides a close-up view of the flowers of 'Baillagone'.

The colors in the photographs are as close as possible with the photographic and printing technology utilized and the color values cited in the Detailed Botanical Description accurately describe the colors of the new *Lagerstroemia*.

DETAILED BOTANICAL DESCRIPTION

The following is a detailed description of 4 year-old plants of the new cultivar as grown outdoors in full sun in a trial garden in Watkinsville, Ga. The phenotype of the new cultivar may vary with variations in environmental, climatic, and cultural conditions, as it has not been tested under all possible environmental conditions. The color determination is in accordance with The 2015 R.H.S. Colour Chart of The Royal Horticultural Society, London, England, except where general color terms of ordinary dictionary significance are used.

General description:

*Blooming period.*—June to September in Watkinsville, Ga., deadheading will result in re-bloom after 8 to 10 weeks.

*Plant type.*—Deciduous flowering shrub.

*Plant habit.*—Compact and upright of intermediate stature, finely textured and dense, freely branched without pruning.

*Height and spread.*—An average of 1.76 m in height and 1.12 m in width.

*Cold hardiness.*—At least in U.S.D.A. Zones 6 to 9.

*Diseases and pests.*—Highly resistant to powdery mildew (caused by *Erysiphe lagerstroemiae*) and Cercospora leaf spot (*Cercospora lythracearum*) has been observed.

*Root description.*—156B in color, young roots are fibrous, older roots become woody.

*Root development.*—An average of 6 weeks at 32° C. for root initiation and an average of 3 months at 32° C. to produce a young rooted plant.

*Propagation.*—Semi-hardwood stem cuttings.

*Growth rate.*—Vigorous.

Branch description:

*Branch shape.*—Tetragonal on first year growth and round on second year growth.

*Branch color.*—First year; 60A in color, second year; 199C, trunk; 199C.

*Branch size.*—Main branches: first year; 24 cm in length, 3 mm in diameter, second year; 45 cm in length, 5 mm in diameter, lateral branches: 50 to 95 cm in length, 1 cm in diameter, trunk; multi-branched and 1.5 cm in diameter at soil level.

*Branch surface.*—Lateral branches moderately covered with coarse irregular lenticels 177C in color, trunk fine barked.

*Branch strength.*—Young; flexible and strong, mature; easily broken.

*Branching.*—Freely branching habit (without pruning), an average of 7 lateral branches.

*Branch aspect.*—Held at angles ranging between 45° to 75°.

*Internode length.*—An average of 1.5 cm.

*Vegetative buds.*—Sub-opposite to alternate in arrangement, an average of 3 mm in length and 2 mm in width, conical in shape, surface imbricate and lacks pubescence, color 138B.

Foliage description:

*Leaf shape.*—Elliptic.

*Leaf division.*—Single.

*Leaf base.*—Cuneate.

*Leaf apex.*—Acuminate.

*Leaf venation.*—Pinnate, upper and lower surfaces 61B in color.

*Leaf margins.*—Entire.

*Leaf arrangement*—Sub-opposite to alternate.

*Leaf attachment.*—Petiolate.

*Leaf surface.*—Both surfaces glabrous and glossy.

*Leaf size.*—An average of 3.5 cm in length and 2 cm in width.

*Leaf quantity.*—An average of 84 per lateral branch.

*Leaf color.*—Young upper surface; 59A, young lower surface; 184B, mature upper surface; NN137C, flushed with 59A, mature lower surface; N138C, flushed with 184B.

*Petiole.*—Average of 1.5 mm in length and 1 mm in diameter, surface texture glabrous, 184A in color, strong.

Flower description:

*Inflorescence type.*—Terminal panicle.

*Lastingness of inflorescence.*—Inflorescences are showy for an average of 2 weeks, individual flowers last an average of 1 day, self cleaning.

*Inflorescence size.*—An average of 19 cm in height and 15 cm in width.

*Inflorescence number.*—One per lateral branch.

*Flower number.*—An average of 50 to 150 flowers and flower buds per inflorescence.

*Flower fragrance.*—Faintly sweet scent.

*Flower buds.*—Globose in shape, an average of 6 mm in length and depth, rounded apex, surface is glabrous with six distinct lines at petal margins, color; N144A with apex 60A.

*Flower aspect.*—Upright to outward.

*Flower type.*—Rotate.

*Flower size.*—An average of 3 cm in height and 3 cm in diameter.

*Petals.*—Typically 7, rotate in arrangement, fan-shaped, ruffled margins, sagittate base, ruffled and rounded apex, both surfaces glabrous, an average of 1 cm in length and width, color when opening and when fully open upper and lower surface; NN155D.

*Calyx.*—Consists of 6 fused sepals, acute apices, an average of 8 mm in length and 1 cm in diameter, N144A in color on both surfaces, smooth and glabrous on both surfaces.

*Peduncles.*—Strong, an average of 7 cm in length and 5 mm in diameter, 59A in color, surface is glabrous with no pubescence, strong.

*Pedicels.*—Strong, an average of 8 mm in length and 1 mm in diameter, 59A in color, surface is glabrous with no pubescence, strong.

Reproductive organs:

*Stamens.*—25 to 30 short stamens clustered in the center, 1.5 mm in length surrounded by 6 longer stamens, 1 cm in length, glabrous surface, anthers; 7A in color, filaments; N155A in color, pollen; moderate in quantity and 7A in color.

*Pistils.*—1, an average of 1.8 cm in length, style; an average of 1.5 cm in length and 39B in color, stigma; round, 1 mm in diameter and 45A in color, ovary; superior, 157A in color and 2 mm in diameter.

*Fruit and seed.*—Capsule; 6-valved, dehiscent, broad ellipsoidal in shape, 7 mm in length and diameter, immature 144A in color, mature N200A in color, each capsule contains 30 seeds an average of 6 mm in length and 3 mm in width and 199B in color.

It is claimed:

1. A new and distinct cultivar of *Lagerstroemia* plant named 'Baillagone' as herein illustrated and described.

* * * * *